(12) United States Patent
Elliott et al.

(10) Patent No.: US 7,906,019 B2
(45) Date of Patent: Mar. 15, 2011

(54) BACTERIA DEACTIVATION APPARATUS

(75) Inventors: David J. Elliott, Wayland, MA (US);
Hem K. Pokharel, Somerville, MA (US)

(73) Assignee: David J. Elliott, Carlisle, MA (US)

( * ) Notice: Subject to any disclaimer, the term of this patent is extended or adjusted under 35 U.S.C. 154(b) by 679 days.

(21) Appl. No.: 11/791,780

(22) PCT Filed: Dec. 5, 2005

(86) PCT No.: PCT/US2005/043950
§ 371 (c)(1),
(2), (4) Date: Dec. 21, 2007

(87) PCT Pub. No.: WO2006/060778
PCT Pub. Date: Jun. 8, 2006

(65) Prior Publication Data
US 2008/0217252 A1 Sep. 11, 2008

Related U.S. Application Data

(60) Provisional application No. 60/633,039, filed on Dec. 3, 2004.

(51) Int. Cl.
*C02F 1/50* (2006.01)
(52) U.S. Cl. .......... 210/205; 210/209; 210/282; 210/501
(58) Field of Classification Search ................ 210/198.1
See application file for complete search history.

(56) References Cited

U.S. PATENT DOCUMENTS

| 3,327,859 | A | 6/1967 | Pall |
| 4,678,571 | A | 7/1987 | Hosaka et al. |
| 5,149,437 | A | 9/1992 | Wilkinson et al. |
| 6,537,939 | B1 | 3/2003 | Harvey |
| 6,712,974 | B1 | 3/2004 | Palm et al. |

OTHER PUBLICATIONS

Ronald J. Gibbs, "Silver Colloids, Do They Work", (ISBN 0-9676992-0-7)(1999).
Dr. Anton Cloete, "All You Need to Know About Colloidal Silver," Revival Nook Centre Of Natural Health.
S. Efrima and B.V. Bronk, "Silver Colloids Impregnating or Coating Bacteria," J. Phys. Chem. B 1998, 102, 5947-5950.
Investigation Of The Potters For Peace Colloidal Silver Impregnated Ceramic Filter, Report 1: Intrinsic Effectiveness, USAID Purchase Order No. 524-0-00-01-00014-5362, 2001.
NSM Products, Nano Silver, http://www.nanosilver.com.my/coated. asp; downloaded from the Internet Sep. 28, 2010, 14 pages.

*Primary Examiner* — Peter A Hruskoci
(74) *Attorney, Agent, or Firm* — Hamilton, Brook, Smith & Reynolds, PC

(57) ABSTRACT

A bacteria deactivation device that has a porous medium through which water and bacteria contained in the water, like *E. coli* and fecal coliform, are passed. Colloidal silver within the medium deactivates bacteria that pass therethrough. The medium has a porosity up to 80% and pores sized to provide flow rates up to 8 liters per hour while meeting Environmental Protection Agency limits for human consumption of silver.

11 Claims, 5 Drawing Sheets

BACTERIA DEACTIVATION APPARATUS

CROSS REFERENCE TO RELATED APPLICATIONS

This application claims priority to U.S. Provisional Application No. 60/633,039, filed Dec. 3, 2004, the entire contents of which are hereby incorporated by reference.

FIELD OF THE INVENTION

This invention relates generally to household or outdoor water systems with high flow rates for use in primitive conditions, and more particularly such a water system that employs methods and devices that purify water by deactivating bacteria through the use of colloidal silver.

RELATED ART

Filters are known for use in treating water. Many filters operate by delivering water that contains bacteria from an unfiltered water chamber, through a porous filter element, and into a filtered water chamber. Pores in the filter element allow water to pass therethrough, but prevent the passage of bacteria, protozoa, and other, smaller pathogens. Such filters purify water by mechanically separating bacteria and retaining the bacteria in the unfiltered water chamber and/or in the filter element itself. Filtered water is collected in the filtered water chamber for subsequent use.

For filters to be effective in removing bacteria, the filter elements should have pores that are smaller than the bacteria that are to be removed. Bacteria, like *E. coli* and fecal coliform, have cross sectional dimensions that range between 1 and 3 microns. Filters that mechanically separate bacteria typically have a pore size of less than 1 micron, which is believed to be an effective size for preventing bacteria, like *E. coli*, and fecal coliform, from passing through a filter element.

Filter elements with smaller pore sizes can prevent the passage of small bacteria, but also require longer periods of time to filter the same amount of water as filter elements with larger pore sizes, all else being constant. Longer filtering times/slower filtration rates are generally undesirable, particularly for simple household water treatment systems that are required for supplying a family with purified water. A typical family of eight persons in a lesser developed country may require upwards of 48 liters of water for drinking and cooking per day, a requirement that may be difficult to satisfy with filters having lower filtration rates, such as filtration rates of 2 liters per hour or less. Longer filtering times are generally also undesirable for other applications, such as camping and hiking, where it is desired to purify as much water as possible in a short period of time.

Filters are known that use suction and/or pressure sources to draw water through a filter element. However, such suction and/or pressure sources can add cost and complexity to the filter. For example, the unfiltered water chamber and/or the filtered water chamber typically must be airtight for a pressure or vacuum source to operate effectively to move water through a filter element. Manufacturing water chambers to be air tight typically requires tighter manufacturing tolerances and additional components for the filter assembly, such as seals and the like. It is generally desirable to produce water treatment devices at lower cost and with less complexity, particularly for applications in lesser developed areas of the world, and particularly for back country use by campers and the like.

Filter elements with smaller pore sizes are more susceptible to being clogged. After continued usage, bacteria and other foreign matter can accumulate on the unfiltered water chamber side of the filter element, or even within the pores of the filter element itself. Continued accumulation of bacteria slows the passage of water through the filter element. In some cases, bacteria that accumulate within the filter can reproduce, thus further blocking the passage of water through the filter element. To remove accumulated bacteria and other debris, filters must be scrubbed clean with a brush or similar implement, or replaced altogether. Scrubbing filters can be a time consuming and undesirable task. Frequent replacement of filter elements adds cost to the maintenance of a filter system. For most applications, there is an interest in preventing the accumulation of bacteria within water treatment devices.

Filters are known that use chemicals to augment the purification of water. Some of such chemicals include chlorine, activated charcoal, fluorine, and colloidal silver. By way of example, Potters For Peace, a United States based non-governmental organization, (www.potpaz.org) has developed a filter with target pore sizes of 1.0 microns in order to remove *e. coli* bacteria. The Potters For Peace filter often is brushed with colloidal silver during manufacturing. Colloidal silver is used in the Potters For Peace filter, in combination with the mechanical separation of bacteria by a filter element, to provide purified water. The Potters For Peace filter has a target flow rate of between 1 and 2 liters per hour, which it is believed is achieved with a filter element that has a porosity of roughly 30%. The flow rate of the Potters For Peace filter is subject to being reduced during use by the build up of contaminants, like bacteria, which may have to be removed by scrubbing the filter element surface.

Colloidal silver is a suspension of fine silver particles in water, and is known for use in killing or deactivating bacteria. The publications *Silver Colloids, Do They Work?*, by Ronald J. Gibbs (ISBN 0-9676992-0-7); *All You Need to Know About Colloidal Silver*, Dr. Anon Cloete, Revival Nook Centre of Natural Health; and *Silver Colloids Impregnating or Coating Bacteria*, S. Efrima and B. V. Bronk, J. Phys. Chem. B1998, 102, 5947-5950, among others, discuss how colloidal silver kills or deactivates bacteria and other pathogens, making the bacteria less harmful to humans. Moreover, the publication *Investigation of the Potters for Peace Colloidal Silver Impregnated Ceramic Filter, Report 1: Intrinsic Effectiveness*, USAID Purchase Order number: 524-0-00-01-00014-5362, discusses the effectiveness of Colloidal Silver used in combination with the filter developed by the Potters for Peace.

There is a need for a water treatment system that does not have the aforementioned drawbacks of conventional filtration systems and that can produce a higher volume flow.

SUMMARY

This invention relates generally to water purification devices that have a porous medium containing colloidal silver. The porous medium has a porosity that allows both water and bacteria to pass therethrough. While resident in the porous medium, bacteria are exposed to and deactivated by colloidal silver also present in the medium. Embodiments of the invention can deactivate about 99.9% of bacteria passing therethrough or greater, which substantially meets World Health Organization standards. Such embodiments also maintain colloidal silver levels below 0.1 mcg/liter which meets Environmental Protection Agency standards for human consumption of silver. Water flow rates up to 8 liters per hour are provided by these embodiments.

In one aspect, this invention relates to a bacteria deactivation device. The bacteria deactivation device comprises a water impermeable receptacle and a porous medium. The porous medium is disposed within the receptacle such that an untreated water compartment lies on an upstream side of said porous medium and a treated water compartment lies on a downstream side of said porous medium. The porous medium has a porosity that allows passage of water and bacteria from said untreated water compartment to said treated water compartment at a water flow rate greater than 2 liters per hour. The bacteria deactivation device also comprises colloidal silver disposed on the porous medium. Bacteria passing from said untreated water compartment to said treated water compartment through said porous medium are exposed to said colloidal silver to deactivate substantially all of the bacteria.

In another aspect, a method of deactivating bacteria within water is disclosed. The method comprises passing water and bacteria in the water from an untreated water compartment, through a porous medium and to a treated water compartment at a water flow rate greater than 2 liters per hour. The method also comprises exposing the bacteria in the water to colloidal silver evident in the porous medium to deactivate the bacteria.

BRIEF DESCRIPTION OF THE FIGURES

The objects, advantages and features of this invention will be more clearly appreciated from the following detailed description, when taken in conjunction with the accompanying drawings, in which.

DETAILED DESCRIPTION

Figure 1:
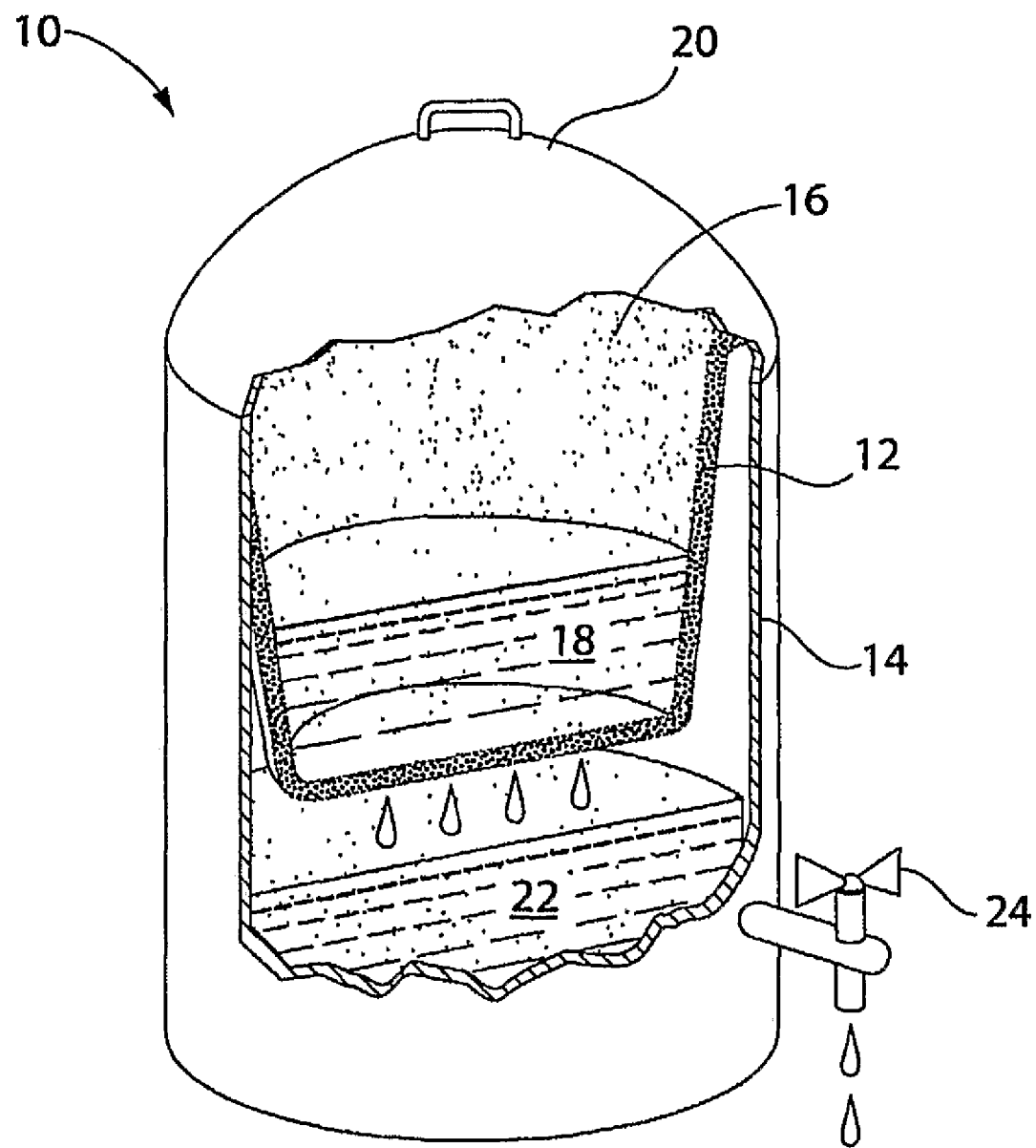
FIG. 1 is a partial, cross-sectional view of one embodiment of a bacteria deactivation device that has a bucket-shaped water impermeable receptacle and a bucket shaped porous medium.

This invention relates to methods and apparatuses for delivering water at high flow rates and under primitive conditions for drinking and cooking in which any bacteria has been deactivated. A porous medium in the bacteria deactivation device has a porosity level sufficiently great to allow passage of water and bacteria, like *E. coli* and fecal coliform at relatively high flow rates. The porous medium is treated with colloidal silver on internal surfaces at concentrations sufficient to deactivate the bacteria, rendering them harmless for human consumption. The porosity level of the porous medium allows the passage of water at rates more than 2 liters per hour and up to 8 liters per hour while providing adequate residence time for deactivation of bacteria passing therethrough. The porosity level also prevents the accumulation of bacteria in the deactivation device, and consequently prevents the flow rate through the porous medium from decreasing substantially over time. "Bacteria" as the term is used herein, refers to pathogens, like *E. coli*, fecal coliform, and other similarly sized pathogens that may be deactivated by exposure to colloidal silver.

Various factors must be considered in making a porous medium used in bacteria deactivation devices of the present invention. Theses factors include the following: colloidal silver concentration, materials used to form the porous medium, methods used to form porosity within the material, the geometric dimensions of the porous medium, hydrostatic pressures present above the porous medium, porosity, average pore size, the necessary structural integrity of the porous medium, and flow rate.

As mentioned above, colloidal silver concentration is a factor that may be considered in designing a deactivation device. Applying too much colloidal silver to a porous medium of a deactivation device may result in treated water that does not meet Environmental Protection Agency standards for the consumption of silver. On the other hand, applying too little colloidal silver may allow substantial amounts of bacteria to pass through a porous medium without being deactivated. Applying too little colloidal silver may also require subsequent reapplication of colloidal silver to maintain the deactivation device in working form. An appropriate amount of colloidal silver can provide a deactivation device that deactivates substantially all bacteria passing therethrough without ever requiring the reapplication of colloidal silver.

The material chosen for the porous medium may affect the structural integrity, the maximum porosity and cost of the resulting porous medium. By way of example, red clay can be used to form a porous medium. Red clay produces an effective, low cost medium as it is readily available, particularly in lesser developed areas. However, when manufactured according to some methods, such as those that result in porosities substantially greater than 80%, porous mediums made from red clay may be too brittle for prolonged use in deactivation devices. Other materials, such as plastic, may prove to have excellent structural properties even at porosities substantially greater than 80%. However, plastic processing equipment is costly and may not be readily available for devices that are to be manufactured in lesser developed areas. Although clay and plastic are mentioned as two types of materials that can be used to form a porous medium, it is to be appreciated that other materials may also be used, as the invention is not limited in this respect.

The method of manufacture can affect several functional aspects of a resulting porous medium. By way of example, a porous medium manufactured from plastic may be expanded through different techniques, such as blowing or mechanically stretching, which may produce different average pore sizes. The extent to which the plastic material is expanded may impact the resulting overall porosity of the porous medium. Similarly, for a porous medium made from clay, the type, size, and amount of combustible material that is added to clay during manufacturing can affect the average pore size, structural strength, and porosity of a resulting porous medium. Generally speaking, larger filler results in larger average pore sizes and greater proportions of filler result in greater porosities. Other facets of the manufacturing process can also affect characteristics of the resulting porous medium.

The external geometry of a porous medium may affect its functional characteristics. By way of example, a porous medium that has a larger external surface area to receive water from an untreated water compartment may be capable of higher volumetric flow rates, all else being constant. A filter medium that is thicker parallel to the flow direction of water through the device, typically results in slower flow rates. This can be due to the additional length that a given bolus of water must travel while passing through the medium. Other geometrical features may be altered to affect characteristics of the porous medium.

The configuration of the water receptacle in which the porous medium resides may also affect functional aspects of a deactivation device. For example, some embodiments may provide for a taller column of water in an untreated water compartment of the device, which can provide a greater hydrostatic pressure at the porous medium. A greater hydrostatic pressure can increase the flow rate through the porous medium, but may also require a structurally stronger porous medium and receptacle to accommodate additional pressure.

Various functional characteristics may have an impact on one another. For example, a porous medium that has a larger average pore size typically also has a larger porosity and may have faster flow rates. Larger porosity can also result in a porous medium that has a larger internal surface area and that may be capable of being doped with an increased amount of colloidal silver. Increased amounts of silver may improve the efficiency of a deactivation device, but on the other hand may increase the concentration of colloidal silver that is delivered to a treated water chamber of the device. Both porosity and average pore size may affect the filtering capabilities of the porous medium. That is, a small average pore size and low porosity may result in a filter element that prevents the passage of bacteria, rather than a porous medium that allows bacteria, like *E. coli* and fecal coliform, to pass therethrough. It is to be appreciated that altering one functional characteristic may impact other characteristics in ways not mentioned above.

FIG. 1 illustrates one embodiment of the invention. The bacteria deactivation device 10 includes a porous medium 12 which may be made from clay or some other material and which may be shaped like a bucket. The porous medium has a typical porosity in the range of 40% to 80%. It is doped with about 5 milliliters of a 3.2% colloidal silver suspension that has been diluted by about 60 parts water to form a 300 milliliter suspension of colloidal silver before being applied to the porous medium. The porous medium 12 may be nested in a water impermeable receptacle 14 that may also be shaped like a bucket. As illustrated, an untreated water compartment 18 is positioned above porous medium 12 and a treated water compartment 22 is positioned below porous medium 12 within receptacle 14, although other configurations are possible. Lid 20 may be used to removably cover the untreated water compartment of the device. Spigot 24 provides a selectively openable passage to allow water to be drawn from the treated water compartment 22.

In use, lid 20 is removed and untreated water is poured through top opening 16 and into untreated water compartment 18 of the embodiment shown in FIG. 1. Lid 20 is then placed over top opening 16 to enclose untreated water compartment 18. Gravity draws water and bacteria within the water from untreated water compartment 18, through porous medium 12, and into treated water compartment 22. The porous structure of porous medium 12 brings water into contact with colloidal silver that has been doped into porous medium 12 through the method discussed above. The colloidal silver deactivates substantially all of the bacteria, such that water collected in the treated water compartment is purified, relative to water in the untreated water compartment and contains less than 0.1 mcg/1 of silver, meeting Environmental Protection Agency Standards.

Figure 2:
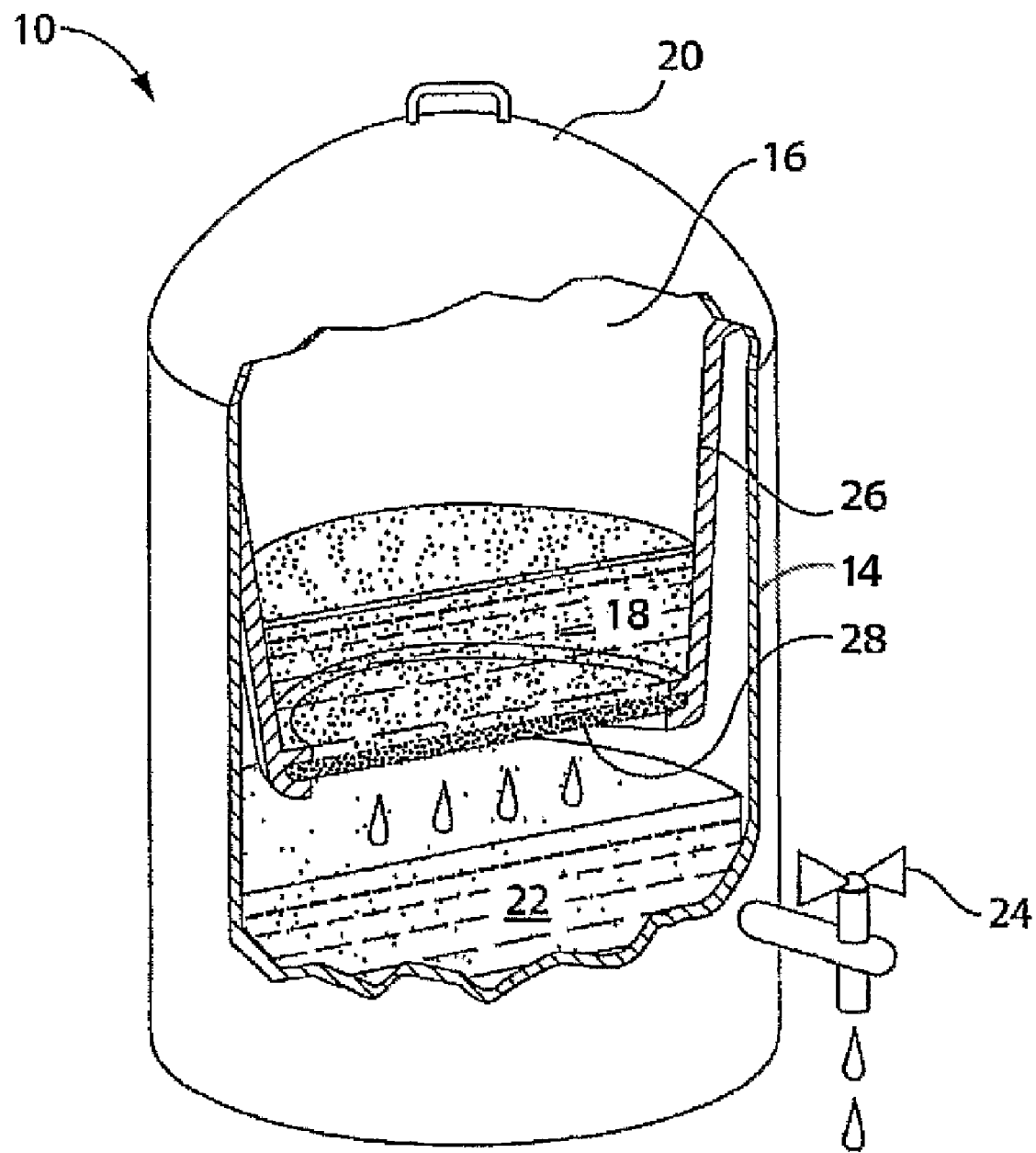
FIG. 2 is a partial, cross-sectional view of another embodiment of a bacteria deactivation device that has a bucket-shaped water impermeable receptacle and a disk shaped porous medium.

A second embodiment of the invention is illustrated in FIG. 2. The second embodiment typically includes a water impermeable receptacle 14 with a lid 20 and spigot 24 similar to those of the first embodiment, although other configurations are possible. The porous medium 12 of the second embodiment comprises a disk 28 that is typically held in water impermeable disk holder 26 in a water tight sealing arrangement. Disk holder 26 is nested within water impermeable receptacle 14, like the porous medium 12 of the first embodiment. Water placed within untreated water compartment 18 of the second embodiment passes only through disk 28 and enters the treated water compartment. In the embodiment of FIG. 2, water does not pass through the walls of the disk holder.

In the illustrated embodiments of FIGS. 1 & 2, the gravity induced hydrostatic pressure of water in untreated water compartment 18 drives the water and bacteria through porous medium 12. The embodiments of FIGS. 1 and 2 typically may be designed to operate with a column of water up to roughly 1 foot. However, embodiments can be configured for use with different heights of water and correspondingly different hydrostatic pressures. If greater hydrostatic pressures are used, adjustments may be made to reduce the porosity and size of the porous medium to achieve desired flow rates, while lower hydrostatic pressures may require lower porosities to achieve the same flow rate.

Illustrative embodiments of the present invention do not necessarily require a pump, such as a pressure pump or a vacuum pump, to drive water through the porous medium. In many embodiments, like those that are used to provide household water in lesser developed areas, a pump may add undesirable costs and complexity to the deactivation device. However, there are applications, such as camping and hiking applications, where adding a pump to the deactivation device may be desirable to increase the flow rate of the deactivation device. In this regard, aspects of the invention are not limited to gravity feed of water.

Figure 3:
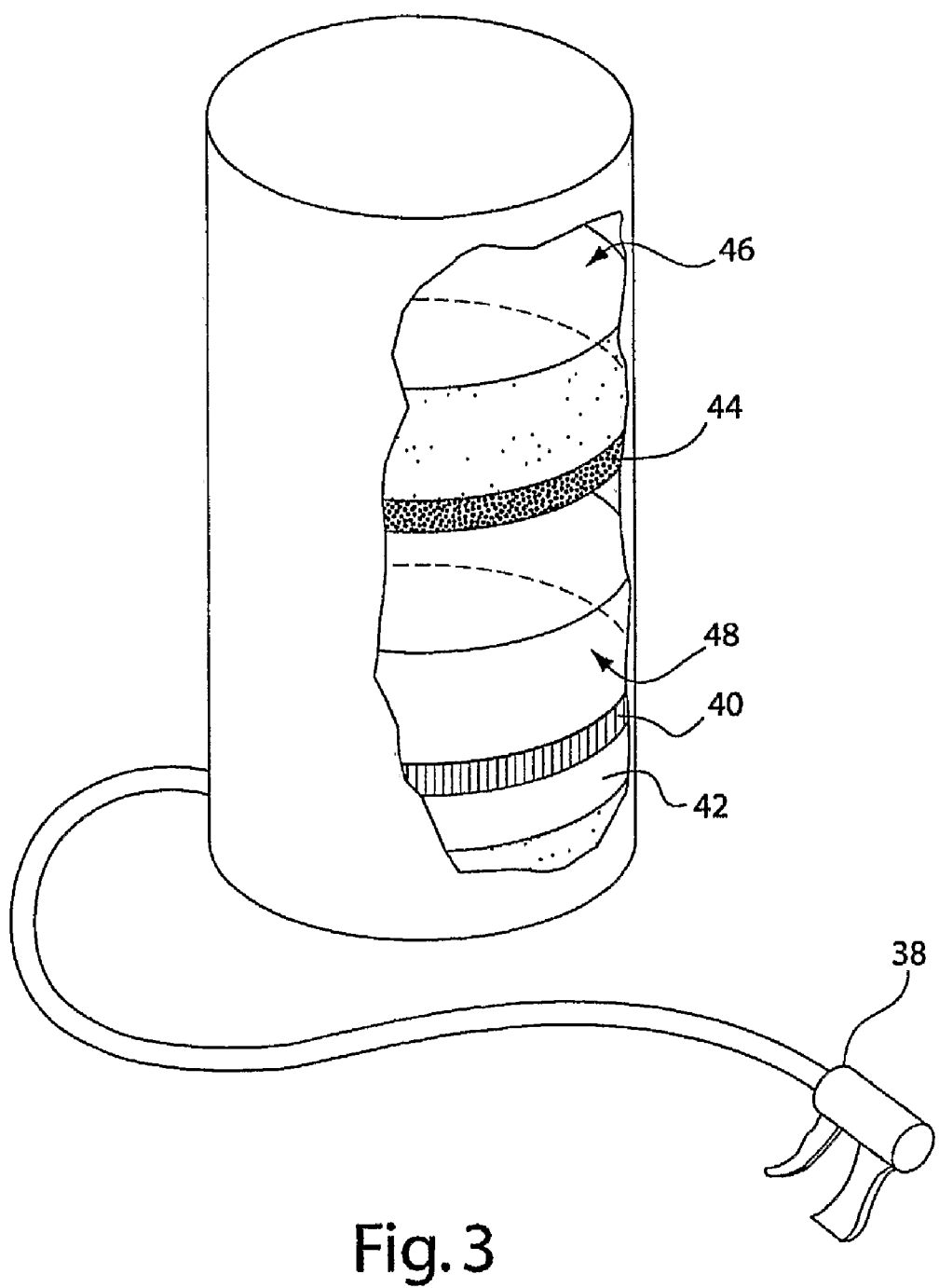
FIG. 3 is a partial, cross-sectional view of yet another embodiment that has a vacuum pump to draw water through a porous medium.

FIG. 3 shows an embodiment of a deactivation device that uses a hand operated vacuum pump 38 to draw water through a disk-shaped porous medium 44. The embodiment of FIG. 3 has both untreated 46 and treated 48 water compartments made from a water impermeable receptacle, which could be made of metal, plastic, or the like. A filter element 40 and filter water compartment 42 are positioned downstream from treated water compartment 48. A vacuum pump 38 draws water from untreated water compartment 46, through porous medium 44 and into treated water compartment 48. The treated water is then drawn by vacuum pump 38 from treated water compartment 22 through filter element 40 and into filtered water compartment 42, where the filtered and treated water may be accessed for use. Such an embodiment may be useful when a portable deactivation device is desired, such as for hiking and camping. Such a device may also be useful in hospitals, where it may be desirable to remove deactivated bacteria from water.

In one example, disk 28 of FIG. 2 may be approximately 8 inches in diameter with an external horizontal surface area facing the untreated water chamber 18 of approximately 50 square inches. The disk may be roughly 1 inch thick and have a porosity just over 30%. A disk with such a configuration typically produces flow rates of just over 2 liters per hour when used as illustrated in FIG. 2. In another illustrative embodiment, a disk 28 is constructed substantially 1 inch thick with a diameter of approximately 8 inches. The disk is manufactured, as described herein, to have a porosity of substantially 70% and pore sizes greater than three microns. This embodiment may produce flow rates up to 8 liters per hour. Porosity can be increased up to 80%, however, the structural strength of a red clay porous disk may be compromised at porosities much greater than 80%. To this end, for embodiments with porosities greater than 80%, alternative materials may be desirable for manufacturing the porous medium.

The amount of colloidal silver in disk 28 is that resulting from the application of 5 ml of 3.2% colloidal silver suspension diluted by 300 ml of water, onto the surface of the porous medium. A suitable commercially available compound may be procured from Spraylat GMBH, of Aachen, Germany. This level of colloidal silver concentration can produce a deactivate device that deactivates 99.9% or greater, 99.99% or greater, or even 100% of bacteria passing therethrough, substantially meeting World Health Organization standards. This embodiment also maintains the colloidal silver level in treated water at or below 0.006 mcg/1, which is below the Environmental Protection Agency limit for human consumption of 0.1 mcg/1. Applying colloidal silver in the above described manner and amount has produced porous medium that do not ever require a reapplication of colloidal silver.

Receptacles, like those shown in the embodiments of FIGS. 1 & 2 can be made of water impermeable clay, or other water impermeable materials. Clay receptacles of FIGS. 1 and 2 can be manufactured through press molding, slip cast molding, coiling of clay, slab rolling of clay, or through an extrusion processes. Alternately, the receptacles can be manufactured of metal, plastic, or even concrete through known methods, as aspects of the invention are not limited in this regard. Similarly, the water impermeable disk holder of the embodiment shown in FIG. 2 can be made through various processes. Ceramic disk holders can be thrown on a potters wheel, slip cast in a mold, formed, extruded or slab rolled. As with the receptacle, the disk holder can be made of different materials, such as metal, plastic, or concrete, as aspects of the invention are not limited to the use of ceramic materials in this regard.

Figure 4:
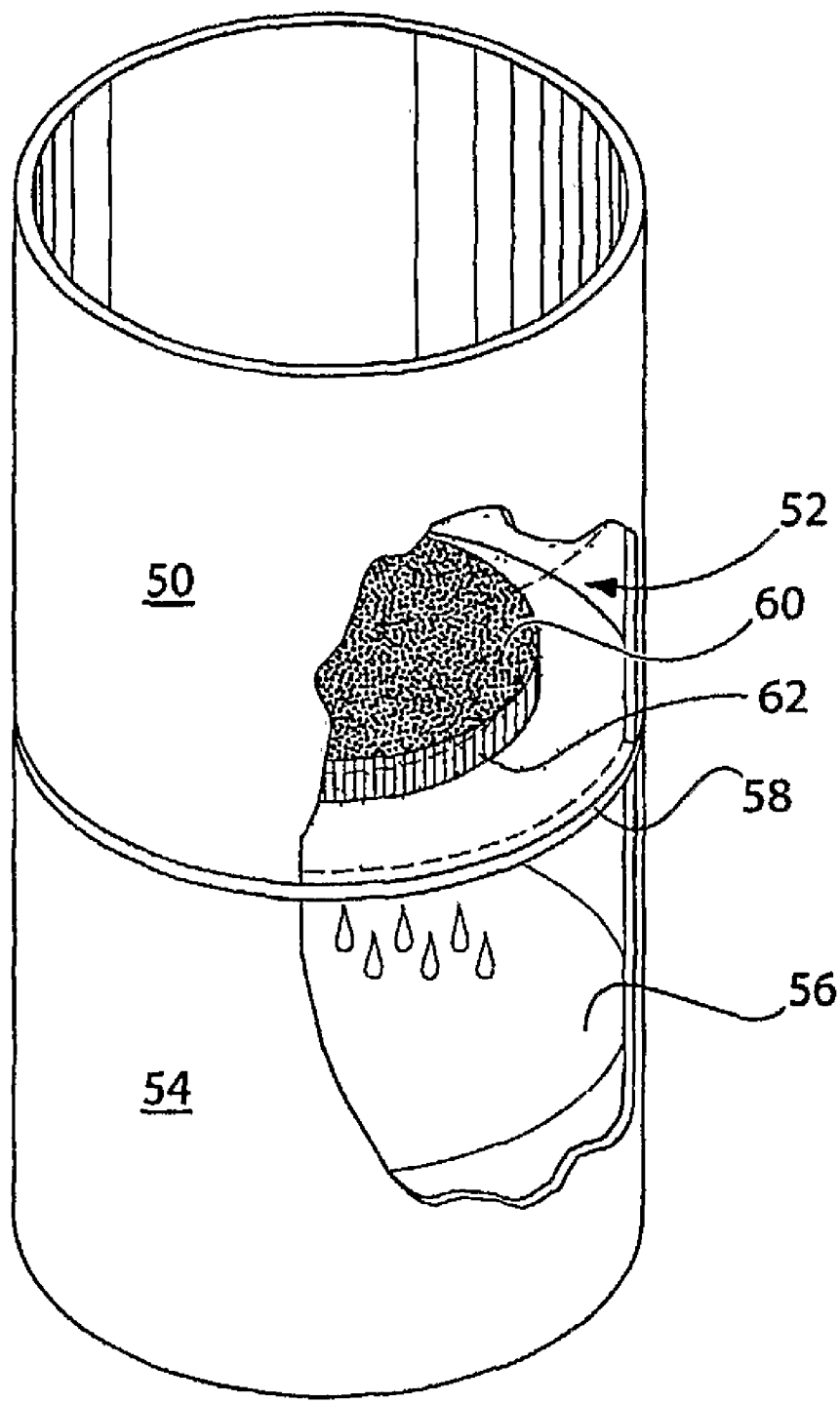
FIG. 4 is a partial, cross-sectional view of another embodiment comprising a disk-shaped porous medium and a pair of water impermeable buckets.

In one embodiment, as shown in FIG. 4, the receptacle comprises a pair of water impermeable buckets, made for example from plastic or metal. A first of the buckets 50 defines an untreated water compartment 52 and a second of the buckets 54 defines a treated water compartment 56. A hole (not shown) is placed in the bottom 58 of the untreated water compartment bucket 50. A porous disk 60, like that described above with respect to FIG. 2, is placed above the hole. The disk, in this embodiment, may be glazed about its peripheral edge 62 to provide a sealing surface. The glazed sealing surface of the disk may be mated to the untreated water compartment bucket 54 in a sealing arrangement. As an example, the porous disk may be mated to a bottom surface of the bucket with silicone aquarium sealer or the like, although aspects of the invention are not limited in this regard. In use, the buckets may be mated to one another such that water is poured into the untreated water bucket, is passed through the porous medium, and is collected in the treated water bucket for subsequent use. Such an embodiment may prove particularly useful in emergency relief situations, such as after a hurricane or earthquake.

As discussed herein, the porous medium 12 may be designed to allow passage of water and bacteria while retaining the bacteria long enough to be deactivated by exposure to colloidal silver resident in the medium. As porosity in the medium is increased in embodiments made of clay, such as through adding additional combustible material to clay during manufacturing, as discussed in greater detail below, the internal surface area of the porous medium increases nonlinearly. Greater internal surface area in the disk can provide for greater exposure between water and bacteria flowing through the porous medium and colloidal silver resident in the porous medium. A greater internal surface area may also provide additional space for the residence of colloidal silver, and thus an increased ability to deactivate bacteria passing therethrough.

As mentioned above, the porosity and pore sizes set forth above have been found to reduce the accumulation of bacteria in the untreated water chamber of the deactivation device by allowing many bacteria to pass through the porous medium. However, some embodiments may have additional features to prevent accumulation of larger pathogens, or contaminants, such as silt and sand. In one embodiment, a filter, such as cheese cloth, may be placed over the opening in the lid when untreated water is poured into the untreated water chamber. This filter removes larger contaminants, like sand and river silt. It is to be appreciated that other materials, like woven or compressed hemp, and other filter membranes may be used in place of cheese cloth, as aspects of the invention are not limited in this regard.

Some embodiments may also have features to remove deactivated bacteria from water that has passed through the porous medium. In one such embodiment, a post filter 40, such as a depth filter, may be positioned downstream of the treated water chamber 48. Water drawn from the treated water chamber 48 may be passed through the filter 40 to remove deactivated bacteria and any other contaminants that may still exist in the treated water. In one embodiment constructed like that of FIG. 3, a sintered nickel depth filter 40 is placed downstream from the treated water compartment 48. However, aspects of the present invention are not limited in this regard, as other types of post filters may be used, or omitted from a device altogether.

In one embodiment, the porous medium may be manufactured as a clay element through potting techniques. Generally, the manufacture of such porous mediums includes the steps of obtaining an appropriate clay and combustible material. The combustible material is used as filler in the clay and is eventually burned away when the clay is fired in a kiln, leaving a porous structure behind. The combustible filler material can be screened to sort out the proper size and amount of filler for the desired porosity of the medium. The filler and the clay are then mixed. The filler and clay mixture is then molded into an appropriate form, such as bucket shaped element for the embodiment of FIG. 1 or a disk shaped element for the embodiment of FIG. 2. The molded clay and filler is allowed to dry and is then fired in a kiln. After firing, the porous medium is soaked in water to provide moisture to the fired clay. Subsequently, the porous medium is bathed in dilute colloidal silver and is then assembled with the remaining components of the bacteria deactivation device.

The porous mediums of the embodiments shown in FIGS. 1 & 2 are often constructed of red clay. Other clays, such as white clay, brown clay or kaolin can be used, but adjustments may need to be made to the type and amount of filler used to achieve desired porosities. The clay may be provided as a dry powder, like Red Art Clay, which can be obtained at most ceramic stores. The clay can also be a wet clay, although dry, powdered clay can facilitate mixing with filler material.

Filler material for the clay often includes sawdust and/or rice husks, although other combustible materials may also be used, such as paper, diatomaceous earth, and the like. The filler may be screened to remove material that is too large, which may result in pores that allow the passage of water too quickly. Screening of sawdust is typically performed with a 30-mesh screener, often made of metal wire. The holes of the screener for sawdust are typically 0.59 inches square to achieve appropriate sized filler for red clay, although different sized screeners may also be used. The holes of the screener for rice husks are often 2.8 mm across, but different sized screeners can be used for rice husks as well.

Once screened, 1 part clay is typically mixed with 3 parts sawdust, or an equivalent amount of an alternate filler material, to achieve porosities of approximately 70%, although other porosities are possible, including porosities between 40% and 80%. Adjustments to the proportions of claim and filler may be made to alter the porosity. The clay is mixed with the filler as 0.75 parts water are slowly added to the mixture. In many embodiments, the filler is evenly mixed throughout the resulting wet clay to provide an even distribution of pores in the resulting porous medium.

A mold and/or a press is used to form the wet clay into the desired shape. Molds may be constructed from a variety of materials, including plaster of paris, metal, cement or even fired clay. The mold for the bucket shaped porous medium can include a male and a female portion that are pressed together with the wet clay mixture therebetween. An operator can press the clay mixture into the mold, taking care to prevent formation of air pockets between the mold and the clay mixture. To prevent the wet clay mixture from sticking to the surface of the mold, a non-adhesive coating, such as a sheet of wax paper, may be placed between the wet clay and the surface of the mold. After the clay mixture is evenly spread about the mold, a mechanically assisted press can be used to form the clay mixture into the appropriate shape within the mold.

After removal from the mold, the wet clay may be allowed to dry, such as in the sun, for between 3 to 7 days, or for a reduced amount of time in a low temperature oven. This initial drying removes some of the moisture from the clay to prevent cracking during the firing process. Once the outer surfaces of the clay mixture have dry appearance, the molded clay can be placed into a kiln for firing.

The firing process can include three different stages: low firing, medium firing and high firing. During low firing, the porous medium is warmed to slowly reduce the moisture content of the clay and prevent cracking, which might occur if the kiln is brought to high temperatures more rapidly. The temperature of the kiln is raised again during the medium firing phase, and once again during the high firing stage, until a temperature of about 1950 degrees Fahrenheit is reached, although lower or higher maximum temperatures can also be acceptable, as aspects of the invention are not limited in this respect. Firing continues, typically until substantially all the combustible material is burned out of the clay. Care should be taken to avoid burning the clay itself, as may be evidenced by black marks, which may impede the passage of fluid through the resulting porous medium.

The porous medium is allowed to cool and is then soaked in water for 8 hours or more to provide moisture to the clay. Subsequently, colloidal silver may be applied to the porous medium. In one approach, 5 ml of 3.2% of colloidal silver suspension is mixed with 300 ml of clean water. A paintbrush is then used to apply diluted colloidal silver in the concentration as set forth above to all surfaces of the porous medium. The colloidal silver is applied until the outer surfaces appear soaked with colloidal silver. In another approach, the porous medium is dipped into diluted colloidal silver in the same concentration as set forth above and allowed to soak for about 5 minutes. After colloidal silver has been applied, the porous medium is allowed to dry for at least 8 hours. Exposure to sunlight should be avoided once the colloidal silver is applied to the porous medium. Colloidal silver is photosensitive and may lose the ability to deactivate bacteria if exposed to sunlight for an extended duration of time.

Once the colloidal silver has dried, the porous medium is assembled to the remaining components of the bacteria deactivation device. In the embodiment shown in FIG. 1, this entails nesting the bucket-shaped porous medium into the water impermeable receptacle. In the embodiment of FIG. 2, the disk-shaped porous medium may be cemented into disk holder 26. Care should be taken to provide a complete seal between the porous disk and the disk holder to prevent untreated water from bypassing the porous medium during device operation.

The water flow rate of the bacteria deactivation device may be measured to check its functionality. Flow rates less than 2 liters per hour may be too low to be adequate. If the flow rate is greater than 8 liters per hour, at least for the embodiments described with respect to FIGS. 1 & 2, the bacteria deactivation device may be deactivating insufficient numbers of bacteria. Examples of porous clay, bucket shaped media as shown in FIG. 1, made with different filler material and with different concentrations of filler material and the resulting flow rates and bacteria deactivation test results are shown below in Table I.

TABLE I

Filter flow rates for different filler materials and percent compositions

| Percent Composition | Filtration rate in ml\hr |
|---|---|
| Sawdust (30%) and Clay (70%) | 15 |
| Sawdust (30%) and Clay (70%) | 20 |
| Sawdust (35%) and Clay (65%) | 110 |
| Sawdust (35%) and Clay (65%) | 95 |
| Sawdust (40%) and Clay (60%) | 200 |
| Sawdust (40%) and Clay (60%) | 210 |
| Sawdust (45%) and Clay (55%) | 340 |
| Sawdust (45%) and Clay (55%) | 350 |
| Sawdust (50%) and Clay (50%) | 100 |
| Sawdust (50%) and Clay (50%) | 80 |
| Sawdust (50%) and Clay (50%) | 100 |
| Sawdust (50%) and Clay (50%) | 100 |
| Sawdust (55%) and Clay (45%) | 200 |
| Sawdust (55%) and Clay (45%) | 150 |
| Sawdust (60%) and Clay (40%) | 400 |
| Whole rice husk (30%) and Clay (70%) | 370 |
| Whole rice husk (30%) and Clay (70%) | 550 |
| Rice husk (20%) and Clay (80%) | 30 |
| Rice husk (20%) and Clay (80%) | 20 |
| Rice husk (20%) and Clay (80%) | 10 |
| Rice husk (25%) and Clay (75%) | 10 |
| Rice husk (25%) and Clay (75%) | 28 |
| Rice husk (30%) and Clay (70%) | 1300 |
| Rice husk (30%) and Clay (70%) | 900 |
| Rice husk (35%) and Clay (65%) | 1250 |
| Rice husk (35%) and Clay (65%) | 1180 |
| Rice husk (40%) and Clay (60%) | 1600 |
| Rice husk (40%) and Clay (60%) | 1400 |
| Rice husk (45%) and Clay (55%) | 1880 |
| Rice husk (45%) and Clay (55%) | 1690 |
| Rice husk (50%) and Clay (50%) | 7400 |
| A Paper (50%) and Clay (50%) | 5 |
| B Paper (50%) and Clay (50%) | Less then 5 |
| C Paper (50%) and Clay (50%) | Less then 5 |
| D Paper (50%) and Clay (50%) | Less then 5 |
| E Paper (50%) and Clay (50%) | Less then 5 |

Presence/absence tests may be performed on water that has passed through a porous medium doped with colloidal silver to provide an indication of whether the porous medium is functioning properly. One such presence/absence test is known as an $H_2S$ bacteria test. In this test, the presence of bacteria is indicated when the test sample turns black (a positive reading), while the absence of bacteria is indicated when the test sample turns yellow (a negative reading). The results of $H_2S$ bacteria tests performed on water that was passed through porous clay, bucket shaped media, as shown in FIG. 1, made with different filler material and with different concentrations of filler material are shown below in Table II.

TABLE II

Results of $H_2S$ bacteria tests

| Percent Composition | Filter # | Results for $H_2S$ Bacteria | Remark |
|---|---|---|---|
| Sawdust (30%) and clay (70%) | 3 | Yellow | Negative |
| Sawdust (30%) and Clay (70%) | 4 | Yellow | Negative |
| Sawdust (35%) and Clay (65%) | 20 | Yellow | Negative |
| Sawdust (35%) and Clay (65%) | 21 | Yellow | Negative |
| Sawdust (40%) and Clay (60%) | 5 | Yellow | Negative |
| Sawdust (40%) and Clay (60%) | 7 | Yellow | Negative |
| Sawdust (45%) and Clay (55%) | 18 | Yellow | Negative |
| Sawdust (45%) and Clay (55%) | 19 | Yellow | Negative |
| Sawdust (50%) and clay (50%) | 1 | Yellow | Negative |
| Sawdust (50%) and clay (50%) | 2 | Yellow | Negative |
| Sawdust (50%) and Clay (50%) | 28 | Yellow | Negative |
| Sawdust (50%) and Clay (50%) | 30 | Yellow | Negative |
| Sawdust (55%) and Clay (45%) | 29 | Yellow | Negative |
| Sawdust (55%) and Clay (45%) | 31 | Yellow | Negative |
| Sawdust (60%) and Clay (40%) | 27 | Yellow | Negative |
| Whole rice husk (30%) and Clay (70%) | 12 | Yellow | Negative |
| Whole Rice husk (30%) and Clay (70%) | 17 | Yellow | Negative |
| Rice husk (20%) and Clay (80%) | 22 | Yellow | Negative |
| Rice husk (20%) and Clay (80%) | 23 | Yellow | Negative |
| Rice husk (20%) and Clay (80%) | 24 | Yellow | Negative |
| Rice husk (25%) and Clay (75%) | 25 | Yellow | Negative |
| Rice husk (25%) and Clay (75%) | 26 | Yellow | Negative |
| Rice husk (30%) and Clay (70%) | 6 | Yellow | Negative |
| Rice husk (30%) and Clay (70%) | 10 | Yellow | Negative |
| Rice husk (35%) and Clay (65%) | 13 | Yellow | Negative |
| Rice husk (35%) and Clay (65%) | 16 | Yellow | Negative |
| Rice husk (40%) and Clay (60%) | 8 | Yellow | Negative |
| Rice husk (40%) and Clay (60%) | 9 | Yellow | Negative |
| Rice husk (45%) and Clay (55%) | 14 | Yellow | Negative |
| Rice husk (45%) and Clay (55%) | 15 | Yellow | Negative |
| Rice husk (50%) and Clay (50%) | 11 | Yellow | Negative |
| Untreated Sudbury River Water | | Black | Positive |
| Untreated Sudbury River Water | | Black | Positive |

Another test that may be used to provide an indication of performance uses HACH Laurly Typtose with Bromcresol Purple broth with MUG reagent to detect the presence or absence of bacteria. Samples subjected to this test will appear murky yellow to the naked eye and will fluoresce under UV light if bacteria are present (a positive reading). If bacteria are not present, the sample will appear purple to the naked eye and will not fluoresce under UV light (a negative reading). The results of such tests performed on samples that were passed through porous clay, bucket shaped media, as shown in FIG. 1, made with different filler material and with different concentrations of filler material are shown below in Table III.

TABLE III

Results of HACH tests

| Percent Composition | Results for Total coliform | Results for E. coli | Remark |
|---|---|---|---|
| Sawdust (30%) and clay (70%) | Purple | No Fluorescence | Negative |
| Sawdust (30%) and Clay (70%) | Purple | e No Fluorescence | Negative |
| Sawdust (35%) and Clay (65%) | Purple | No Fluorescence | Negative |
| Sawdust (35%) and Clay (65%) | Purple | No Fluorescence | Negative |
| Sawdust (40%) and Clay (60%) | Purple | No Fluorescence | Negative |
| Sawdust (40%) and Clay (60%) | Purple | No Fluorescence | Negative |
| Sawdust (45%) and Clay (55%) | Purple | No Fluorescence | Negative |
| Sawdust (45%) and Clay (55%) | Purple | No Fluorescence | Negative |
| Sawdust (50%) and clay (50%) | Purple | No Fluorescence | Negative |
| Sawdust (50%) and clay (50%) | Purple | No Fluorescence | Negative |
| Sawdust (50%) and Clay (50%) | Purple | No Fluorescence | Negative |
| Sawdust (50%) and Clay (50%) | Purple | No Fluorescence | Negative |
| Sawdust (55%) and Clay (45%) | Purple | No Fluorescence | Negative |
| Sawdust (55%) and Clay (45%) | Purple | No Fluorescence | Negative |
| Sawdust (60%) and Clay (40%) | Purple | No Fluorescence | Negative |
| Whole rice husk (30%) and Clay (70%) | Purple | No Fluorescence | Negative |
| Whole Rice husk (30%) and Clay (70%) | Purple | No Fluorescence | Negative |
| Rice husk (20%) and Clay (80%) | Purple | No Fluorescence | Negative |
| Rice husk (20%) and Clay (80%) | Purple | No Fluorescence | Negative |
| Rice husk (20%) and Clay (80%) | Purple | No Fluorescence | Negative |
| Rice husk (25%) and Clay (75%) | Purple | No Fluorescence | Negative |
| Rice husk (25%) and Clay (75%) | Purple | No Fluorescence | Negative |
| Rice husk (30%) and Clay (70%) | Purple | No Fluorescence | Negative |
| Rice husk (30%) and Clay (70%) | Purple | No Fluorescence | Negative |
| Rice husk (35%) and Clay (65%) | Purple | No Fluorescence | Negative |
| Rice husk (35%) and Clay (65%) | Purple | No Fluorescence | Negative |
| Rice husk (40%) and Clay (60%) | Purple | No Fluorescence | Negative |
| Rice husk (40%) and Clay (60%) | Purple | No Fluorescence | Negative |
| Rice husk (45%) and Clay (55%) | Purple | e No Fluorescence | Negative |
| Rice husk (45%) and Clay (55%) | Purple | No Fluorescence | Negative |
| Rice husk (50%) and Clay (50%) | Purple | c Fluorescence | Negative |
| Untreated Sudbury River Water | Murky Yellow | Fluorescence | Positive |
| Untreated Sudbury River Water | Murky Yellow | Fluorescence | Positive |

A membrane filtration test may also be performed to provide a qualitative indication as to how well a deactivation device is performing. In membrane filtration tests, water samples that have been passed through a porous medium are passed through a membrane that collects bacteria. The membrane is then placed in an environment where any bacteria that are present will be cultured into colony forming units. Resulting bacteria colony forming units can subsequently be viewed under a stereoscope and counted to provide an indication of device performance. In *E. coli* and total coliform tests, *E. coli* bacteria will be present as blue colony forming units and total coliforms will be present as red bacteria colony forming units. In fecal coliform tests, fecal coliform will be present as blue colony forming units. The colonies can be counted and compared with the number of colonies present in an untreated sample to calculate a percent removal efficiency. The results of membrane filtration tests performed on samples that were passed through porous clay, bucket shaped media, as shown in FIG. 1, made with different filler material and with different concentrations of filler material are shown below in Tables IV and V.

TABLE IV

Results of membrane filtration test for *e. coli* and total coliform

| Percent Composition | Sample Volume in ml. | Blue colonies | Red Colonies | Total Colonies | % Efficiency of filter for Total Coliform and *E. Coli* |
|---|---|---|---|---|---|
| Rice husk (30%) and Clay (70%) | 100 | None | None | None | 99.98 |
| Rice husk (30%) and Clay (70%) | 100 | None | None | None | 99.98 |
| Rice husk (35%) and Clay (65%) | 100 | None | None | None | 99.98 |
| Rice husk (35%) and Clay (65%) | 100 | None | None | None | 99.98 |
| Rice husk (40%) and Clay (60%) | 100 | 1 | 1 | 2 | 99.97 |
| Rice husk (40%) and Clay (60%) | 100 | 1 | 2 | 3 | 99.96 |
| Rice husk (45%) and Clay (55%) | 100 | None | None | None | 99.98 |
| Rice husk (45%) and Clay (55%) | 100 | None | 3 | 3 | 99.96 |
| Rice husk (50%) and Clay (50%) | 100 | 1 | 5 | 6 | 99.92 |
| Untreated Sudbury River Water | 100 | | | 8140 | ? |
| Untreated Sudbury River Water | 5 | | | 407 | ? |

TABLE V

Results of membrane filtration test for fecal coliform

| Filter # & Percent Composition | Total Blue Colonies | Remark for the Test |
|---|---|---|
| Sawdust (30%) and Clay (70%) | 0 | Negative |
| Sawdust (30%) and Clay (70%) | 0 | Negative |
| Sawdust (40%) and Clay (60%) | 0 | Negative |
| Sawdust (40%) and Clay (60%) | 0 | Negative |
| Sawdust (45%) and Clay (55%) | 0 | Negative |
| Sawdust (50%) and Clay (50%) | 0 | Negative |
| Sawdust (50%) and Clay (50%) | 0 | Negative |
| 6. Rice husk (30%) and Clay (70%) | 0 | Negative |
| 10. Rice husk (30%) and Clay (70%) | 0 | Negative |
| 13. Rice husk (35%) and Clay (65%) | 0 | Negative |
| 16. Rice husk (35%) and Clay (65%) | 0 | Negative |
| 8. Rice husk (40%) and Clay (60%) | 0 | Negative |
| 9. Rice husk (40%) and Clay (60%) | 3 | Positive |
| 14. Rice husk (45%) and Clay (55%) | 0 | Negative |
| 15. Rice husk (45%) and Clay (55%) | 3 | Positive |
| 11. Rice husk (50%) and Clay (50%) | 5 | Positive |
| 12. Whole rice husk (30%) and Clay (70%) | 0 | Negative |
| 17. Whole rice husk (30%) and Clay (70%) | 0 | Negative |
| Untreated Sudbury River Water | 127 | Positive |

Tests were also performed on water passed through an embodiment constructed like that of FIG. 2 with a disk-shaped porous medium disk having a one inch thickness and a diameter of 8 inches. Samples were collected from devices with flow rates of both 4.5 liters per hour and 7.5 liters per hour exhibited zero bacteria (i.e., fecal coliform and *E. coli*), as confirmed through tests performed by Nepal Environmental & Scientific Services.

Figure 5:
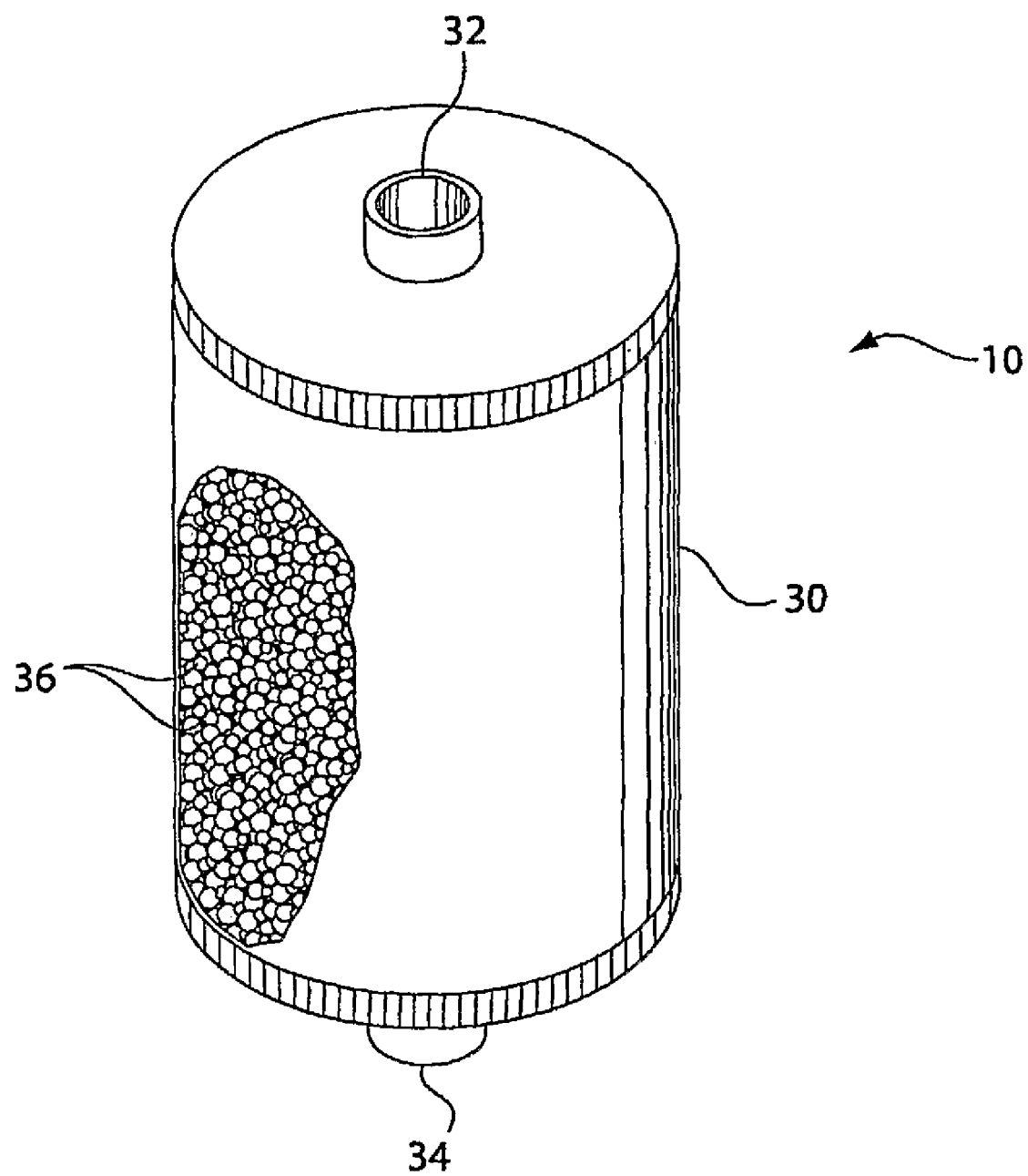
FIG. 5 is a partial, cross-sectional view of a still another embodiment of a bacteria deactivation device that has a cylinder shaped water impermeable receptacle and a porous medium comprising loose particles disposed inside the cylinder.

FIG. 5 illustrates a yet another embodiment of a bacteria deactivation device. This embodiment includes a canister-shaped, water impermeable receptacle 30. Receptacle 30 has an inlet 32 that receives water from an untreated water compartment 18 and an outlet 34, through which water is delivered to a treated water compartment 22. Particles 36 of pumice or other porous media that are coated with colloidal silver are disposed in canister 30 to provide a porous medium through which water and bacteria can travel. Water and bacteria are received through inlet 32, travel through the interstices between particles 36 in canister 30, where the bacteria are exposed to colloidal silver for deactivation. The water and bacteria continue to move toward the outlet, out of the canister, and into a treated water compartment for subsequent use.

The porous medium in the embodiment of FIG. 5 is not a defined by a single mass, but rather by a collection of loose particles or beads 36 within water impermeable receptacle 30.

Colloidal silver is applied to particles 36, either by brushing or soaking, prior to the particles being inserted into canister 30. Flow rates and residence times through the canister can be adjusted. By way of example, a longer canister may provide for longer residence times and slower flow rates. A canister with smaller beads will have a lower porosity, which will result in greater residence time and slower flow rates. A canister with a larger cross sectional area (taken in a direction that lies orthogonal to the direction that water flows through the canister), will typically produce greater flow rates. These factors can be manipulated to provide a canister configuration that will deactivate an acceptable level of bacteria with a desirable flow rate, such as a flow rate above 2 liters per hour, above 4 liters per hour, and up to 8 liters per hour.

Having thus described several aspects of at least one embodiment of this invention, it is to be appreciated that various alterations, modifications and improvements will readily occur to those skilled in the art. Such alterations, modifications and improvements are intended to be part of this disclosure, and are within the spirit and scope of the invention. Accordingly, the description and drawings are by way of example only. The invention is intended to be limited only by the following claims and their equivalents.

What is claimed is:
1. A bacteria deactivation device comprising:
a water impermeable receptacle;

a porous medium disposed within said receptacle such that an untreated water compartment lies on an upstream side of said porous medium and a treated water compartment lies on a downstream side of said porous medium, said porous medium having a porosity that allows passage of water and bacteria from said untreated water compartment to said treated water compartment at a water flow rate greater than 4 liters per hour;

and colloidal silver disposed on said porous medium such that bacteria passing from said untreated water compartment to said treated water compartment through said porous medium are exposed to said colloidal silver to deactivate substantially all of said bacteria wherein said porous medium has a porosity greater than 40%, and a pore size greater than 3 microns, to prevent accumulation of bacteria in said deactivation device.

2. The bacteria deactivation device of claim 1, wherein said water flow rate is up to 8 liters per hour.

3. The bacteria deactivation device of claim 1, wherein said porous medium has a porosity up to 80%.

4. The bacteria deactivation device of claim 1, wherein said water flow rate is achieved under hydrostatic pressure associated with one foot or less of water in said untreated water compartment.

5. The bacteria deactivation device of claim 1, wherein said water flow rate is achieved with less than about 50 square inches of external surface area of said porous medium being directly exposed to said untreated water compartment.

6. The bacteria deactivation device of claim 1, wherein pores in said porous medium are sized to allow passage of bacteria having diameters up to 5 microns from said untreated water compartment to said treated water compartment.

7. The bacteria deactivation device of claim 1, wherein said bacteria are selected from a group consisting of fecal coliform and *E. Coli*.

8. The bacteria deactivation device of claim 1, wherein said water impermeable receptacle comprises a water impermeable bucket.

9. The bacteria deactivation device of claim 8, wherein said porous medium comprises a porous red clay bucket nested within said water impermeable bucket, said untreated water compartment being defined within said porous red clay bucket and said treated water compartment being defined between said water impermeable bucket and said porous red clay bucket.

10. The bacteria deactivation device of claim 8, wherein said porous medium comprises a porous red clay disk fastened to a bucket shaped disk holder, said bucket shaped disk holder nested within said water impermeable bucket, said untreated water compartment being defined within said bucket shaped disk holder and said treated water compartment being defined between said water impermeable bucket and said bucket shaped disk holder.

11. The bacteria deactivation device of claim 1, wherein said water impermeable receptacle comprises a canister having an inlet and an outlet and further wherein said porous medium comprises beads of pumice disposed within said canister, said untreated water compartment lying upstream of said inlet and said treated water compartment lying downstream of said water outlet.

* * * * *